United States Patent
Tschopp et al.

(10) Patent No.: US 10,441,456 B2
(45) Date of Patent: Oct. 15, 2019

(54) IMPLANT

(75) Inventors: Kurt Tschopp, Liestal (CH); Michael Breitenstein, Wenslingen (CH)

(73) Assignee: MEDARTIS AG, Basel (CH)

( * ) Notice: Subject to any disclaimer, the term of this patent is extended or adjusted under 35 U.S.C. 154(b) by 1216 days.

(21) Appl. No.: 12/632,005

(22) Filed: Dec. 7, 2009

(65) Prior Publication Data
US 2010/0163056 A1 Jul. 1, 2010

(30) Foreign Application Priority Data

Dec. 30, 2008 (EP) .................................... 08106040

(51) Int. Cl.
*A61F 5/56* (2006.01)

(52) U.S. Cl.
CPC .................................... *A61F 5/566* (2013.01)

(58) Field of Classification Search
CPC .................................... A61F 5/56; A61F 5/566
USPC .................. 128/848; 600/9, 12; 623/9, 11.11
See application file for complete search history.

(56) References Cited

U.S. PATENT DOCUMENTS

| | | | | |
|---|---|---|---|---|
| 6,401,717 B1 * | 6/2002 | Conrad | | A61F 5/566 128/897 |
| 6,899,105 B2 | 5/2005 | Krueger | | |
| 7,213,599 B2 | 5/2007 | Conrad | | |
| 7,237,554 B2 | 7/2007 | Conrad | | |
| 7,337,781 B2 | 3/2008 | Vasallo | | |
| 7,401,611 B2 | 7/2008 | Conrad | | |
| 8,307,831 B2 * | 11/2012 | Rousseau | | 128/848 |
| 2005/0065615 A1 | 3/2005 | Krueger | | |
| 2005/0154412 A1 | 7/2005 | Krueger | | |
| 2006/0185680 A1 * | 8/2006 | Bhat et al. | | 128/848 |
| 2006/0201519 A1 | 9/2006 | Frazier | | |
| 2006/0207606 A1 | 9/2006 | Roue | | |
| 2006/0207607 A1 | 9/2006 | Hirotsuka | | |
| 2006/0207608 A1 | 9/2006 | Hirotsuka | | |
| 2006/0207612 A1 | 9/2006 | Jackson | | |
| 2006/0235380 A1 | 10/2006 | Vasallo | | |
| 2007/0000497 A1 * | 1/2007 | Boucher et al. | | 128/848 |
| 2007/0227545 A1 | 10/2007 | Conrad | | |
| 2007/0233276 A1 | 10/2007 | Conrad | | |

(Continued)

FOREIGN PATENT DOCUMENTS

EP 1216013 6/2006
EP 2 356 954 A1 * 8/2011

(Continued)

*Primary Examiner* — Kari K Rodriquez
*Assistant Examiner* — Camtu T Nguyen
(74) *Attorney, Agent, or Firm* — Davis & Bujold PLLC; Michael J. Bujold (57) ABSTRACT

The invention relates to an implant for a palate, in particular a human palate. The implant comprises a proximal portion, a distal portion and a middle portion. The proximal portion is dimensioned in such a way that it can be fixed to a hard palate. The distal portion is arranged at an angle in relation to the proximal portion and is dimensioned in such a way that it can be accommodated completely in a soft palate. The middle portion extends between the proximal portion and the distal portion. In a sectional plane extending through the proximal portion and the distal portion, the curvature of the middle portion at each of its points is greater than the curvature of the proximal portion at each of its points and greater than the curvature of the distal portion at each of its points.

15 Claims, 11 Drawing Sheets

(56) References Cited

U.S. PATENT DOCUMENTS

| | | |
|---|---|---|
| 2008/0023012 A1 | 1/2008 | Dineen |
| 2008/0027560 A1 | 1/2008 | Jackson |
| 2008/0035160 A1 | 2/2008 | Woodson |
| 2008/0053461 A1 | 3/2008 | Hirotsuka |
| 2008/0058584 A1 | 3/2008 | Hirotsuka |
| 2008/0066769 A1 | 3/2008 | Dineen |
| 2008/0078411 A1 | 4/2008 | Buscemi |
| 2008/0078412 A1 | 4/2008 | Buscemi |
| 2008/0097380 A1 | 4/2008 | Li |
| 2008/0208265 A1 | 8/2008 | Frazier |

FOREIGN PATENT DOCUMENTS

| | | |
|---|---|---|
| WO | 01/45571 | 6/2001 |
| WO | 2007/095582 | 8/2007 |

* cited by examiner

IMPLANT

The present invention relates to an implant for a palate, in particular a human palate, to a set of implants and to a selection process for selecting an implant according to the preambles of the independent patent claims.

Approximately 2-4% of the world's population of middle age suffer from obstructive sleep apnea syndrome (OSAS). The patients affected by this suffer from relaxations in the area of the throat and neck, which lead to usually brief interruptions in breathing, which under some circumstances are repeated several hundred times per night. Obstructive sleep apnea is a risk factor for cardiovascular disorders such as heart attacks or strokes. Frequent interruptions in breathing may in the worst case lead to sudden death by cardiac arrest or cerebral apoplexy. Arousal reactions may be mentioned as a further consequence of interrupted breathing, leading to disturbed, fragmented sleep without phases of deep sleep. This has the consequence that the patients are not fully rested in the morning and complain of increased daytime fatigue. So-called microsleep, which may occur for example during car driving, is particularly dangerous. For instance, the risk of a fatal car crash is seven times greater in the case of patients with OSAS than in the case of the normal population.

Snoring is also based on similar anatomical conditions, namely a constriction of the airways during sleep. However, the collapse of the airways is not complete, but only partial, with the result that only snoring noises are produced, but there is no drop in the oxygen blood levels or arousal reaction. Although snoring does not endanger the actual patient, those around may suffer.

The collapse of the airways may be caused either by closing at the palate or by falling back of the tongue. To treat the condition, for some time implants which are inserted either into the soft part of the palate or into the base of the tongue have been used. Such an implant that can be inserted into the soft palate is described, for example, in EP 1 216 013. This implant consists of polyester fibers braided together. If one or more of these implants is inserted into the soft palate of the patient, this leads to a stiffening of the soft palate. This is intended to change the dynamic response of the soft palate in such a way that a fluttering movement such as that which occurs during snoring and the falling back of the soft palate when the patient is in a lying position can be prevented.

However, this implant that is known from the prior art has a series of disadvantages. This is so since, even if the entire soft palate is stiffened, it can nevertheless undergo a fluttering movement as a whole and also fall back as a whole into the area of the throat when the patient is in a lying position, which can lead to dangerous interruptions in breathing.

It is therefore an object of the present invention to overcome the disadvantages from the prior art and, in particular, to provide an implant for a palate which effectively suppresses the fluttering movements of the palate that lead to snoring and also prevents falling back of the soft palate, without for example hindering speaking or swallowing.

This object is achieved by an implant, a set of implants and a process with the features of the characterizing parts of the independent patent claims. The implant is suitable for a palate, in particular a human palate. It comprises a distal portion, which is dimensioned in such a way that it can be completely accommodated in a soft palate. The term "distal" refers to the position of the portion when the implant is inserted as intended into a palate.

According to the invention, the implant further comprises a proximal portion, which is dimensioned in such a way that it can be fixed to a hard palate. The term "proximal" also refers to the position when the implant is inserted as intended into a palate. Moreover, the implant has a middle portion, which extends between the proximal portion and the distal portion.

An implant according to the invention may be inserted into a palate by fixing the proximal portion to a hard palate, in particular along the entire length of the proximal portion. The distal portion may be inserted completely into a soft palate. On account of the fixing to the hard palate, at least the proximal portion, in particular the entire palate, can be secured at a substantially stable angle in relation to the hard palate. The distal portion serves for stiffening the soft palate and restricts a fluttering movement or other movement of the soft palate.

On account of the fixing of the proximal portion to the hard palate, the movement of the soft palate as a whole in relation to the hard palate is also additionally restricted. The implant according to the invention consequently serves effectively for lengthening the hard palate and for assuming a natural rest position, unless the soft palate is brought into another position by the tensioning of the musculature of the palate. Consequently, the risk of the soft palate falling back when the patient is in a lying position is significantly reduced in comparison with the prior art.

The implant may either be already in an inserted form or can at least be brought into an inserted form. The inserted form is understood in this case as meaning the form of the implant when it is inserted as intended into a palate and the proximal portion is thereby fixed to the hard palate and the distal portion is completely accommodated in the soft palate. At least in this inserted form, the distal portion can be arranged at an angle in relation to the proximal portion.

In a sectional plane extending through the proximal portion and the distal portion, the middle portion may have a curvature at every point. A curvature at a point of the implant is understood here and hereafter as meaning the inverse value of the radius of an imaginary osculating circle which osculates the middle portion at this point. Such a curvature therefore has the dimension of an inverse length.

With preference, at least in the inserted form of the implant, the curvature of the middle portion in the sectional plane is at each of its points greater than the curvature of the proximal portion at each of its points. The curvature of the proximal portion and the curvature of the distal portion are defined in the same way as the curvature of the middle portion.

In other words, the implant therefore preferably comprises two portions (a proximal portion and a distal portion), which, at least in the inserted form of the implant, have a smaller curvature than a middle portion extending between them.

In particular, it is possible and within the scope of the above definition, that, at least in the inserted form, the proximal portion and/or the distal portion is/are straight, i.e. uncurved; in this case, each point of the proximal portion and/or of the distal portion is assigned a curvature of zero. Furthermore, it is within the scope of the above definition that, at least in the inserted form, the middle portion comprises at least one kink or consists of at least one kink. A kink is formally assigned a curvature of infinity.

The matching of the curvatures of the proximal, distal and middle portions in the inserted form has the effect that the proximal portion and/or the distal portion can follow an uncurved and/or only slightly curved path and, consequently, correspond to the anatomy of the hard palate or of the soft palate. The middle portion of the implant may be arranged in the vicinity of the transition from the hard palate to the soft palate, where the anatomy naturally prescribes a greater curvature.

With preference, in the inserted form, the curvature of the proximal portion in the sectional plane is at each point at most 1 cm$^{-1}$, preferably 0.5 cm$^{-1}$, particularly preferably at most 0.2 cm$^{-1}$. Furthermore, with preference, in the inserted form, the curvature of the distal portion in the sectional plane is at each point at most 1 cm$^{-1}$, preferably at most 0.5 cm$^{-1}$, particularly preferably at most 0.2 cm$^{-1}$. In particular, the proximal and/or distal portions may be straight in the inserted form; according to the above definition, there is then a curvature of zero.

Likewise with preference, in the inserted form, the middle portion has at each point a curvature of at least 2 cm$^{-1}$, preferably at least 10 cm$^{-1}$, particularly preferably at least 100 cm$^{-1}$. In particular, in the inserted form, the middle portion may at one point have a kink; within the scope of the above definition, this point is then assigned a curvature of infinity.

In some embodiments, the implant is formed in such a way that it may not only take the inserted form but also a ready form, from which it can be brought into the inserted form. In the ready form, the implant has qualitatively different curvature properties than in the inserted form. For example, in the ready form it may be flat, that is to say completely uncurved. In this ready position, the implant can, for example, be packed more easily and/or be inserted more easily.

In some embodiments, the middle portion may have an intended deformation region, in which the middle portion can be deformed, in particular plastically deformed, in particular can be bent and/or can be kinked. In this way, a preferred position of the implant at which it can be bent and/or kinked is defined. The implant can then be brought from the ready form, in which for example the implant could be flat, into the inserted form by deformation of the intended deformation region. With preference, the intended deformation region comprises at least one constriction, at which the middle portion can be bent or can be kinked.

In some embodiments, the implant may comprise a shape memory material, in particular NITINOL, or consist thereof. Such an implant may, for example, be formed in such a way that, at a ready temperature, it is in the ready form and, at an inserted temperature, it is in the inserted form. Accordingly, the inserted temperature coincides with the normal human body temperature and is therefore preferably between 35° C. and 40° C., particularly preferably between 36° C. and 37° C. The ready temperature may be higher or lower than the inserted temperature. At a ready temperature, the implant may be in such a ready form in which it can be inserted particularly easily into a palate, for example in a flat form. On account of the change in temperature that the implant undergoes during insertion, it then assumes the inserted form of its own accord. The production of implants that comprise a shape memory material and assume a predefined form when there is a change in temperature is known per se to a person skilled in the art and is described, for example, in WO 01/45571.

NITINOL has resilient and anticorrosive properties that are advantageous for the purposes of the invention and, moreover, is authorized as a medical material. NITINOL is available in various configurations and compositions, which differ for example with regard to their densities or flexibilities. By conducting routine tests, a person skilled in the art can select the composition that is suitable on the basis of the dimensions and resilient properties that are required within the scope of invention.

In preferred embodiments, in the inserted form, the distal portion is arranged in relation to the proximal portion at an angle of between 15° and 75°, preferably between 20° and 60°, particularly preferably between 30° and 50°. These angular ranges correspond to the usual angles between the hard palate and the soft palate that are prescribed by the human anatomy.

With particular preference, the implant is at least partially elastic in such a way that the distal portion is resilient in relation to the proximal portion. In particular, the implant may be elastic in the middle portion in such a way that the distal portion is resilient in relation to the proximal portion. This makes it possible for the soft palate to be able to move to a certain extent in relation to the hard palate when the implant is inserted as intended. On the one hand, this prevents the soft palate from falling back when the patient is in a lying position, while on the other hand it also does not excessively restrict speaking and swallowing for example. With preference, the implant is elastic in such a way that the pressures typically occurring behind the soft palate during swallowing, of approximately 50-100 cm water column, can still be overcome by an average palate musculature. The implant according to the invention does not simply have a stiffening effect, but gives the soft palate increased tension, and guides the soft palate into a natural rest position, similar to that achieved by the soft palate itself in people without OSAS.

According to a preferred embodiment, the implant is substantially in the form of a strip. An implant in the form of a strip can be implanted particularly easily into a palate.

According to preferred embodiments, a proximal end of the proximal portion and/or a distal end of the distal portion is/are rounded. In this way it is possible to avoid sharp edges, which could lead to unintentional injuries of the palate when the implant is inserted or could be troublesome for the patient later. In particular, the proximal end and/or the distal end could be rounded within a plane which extends perpendicularly to a sectional plane which, in the inserted form, extends through the proximal portion and the distal portion.

With preference, the proximal portion has a length of 15 mm to 30 mm, preferably of 20 mm to 25 mm. The length of the proximal portion is understood as meaning its extent in the direction of the middle portion and in a central sectional plane which extends through the proximal portion and the distal portion. Such a length of the proximal portion on the one hand makes adequate fixing to the hard palate possible, in particular if the proximal portion is fixed to the hard palate along its entire length. On the other hand, the length of the proximal portion is thereby chosen in such a way that it is not considered by the patient to be excessively troublesome.

With further preference, the distal portion has a length of 15 mm to 25 mm, preferably of 18 mm to 22 mm, particularly preferably of 19 mm to 21 mm. The length of the distal portion is also understood as meaning its extent in the direction of the middle portion and in a central sectional plane which extends through the proximal portion and the distal portion. A distal portion with such a length is adapted to the soft palate in the parauvular region of an adult patient with average anatomy.

In the case of implants intended for medial insertion up to or into the uvula, the distal portion preferably has a length of 15 mm to 35 mm, particularly preferably of 20 mm to 30 mm.

Likewise with preference, the implant has a width of between 1 mm and 8 mm, preferably between 1.5 mm and 5.5 mm, particularly preferably between 2 mm and mm. The width of the implant is understood as meaning perpendicularly to a sectional plane which extends through the proximal portion and the distal portion.

Likewise with preference, the implant has a thickness of 0.02 mm to 3 mm, which is chosen in dependence on the material of the implant (see below). The thickness is in this case the extent of the implant perpendicularly to the extent of the length defined above and in a sectional plane which, in the inserted form, extends through the proximal portion and the distal portion.

In the case of some embodiments, the thickness of the implant may decrease at least in the distal portion in the direction of a distal end of the implant. This form of the implant is particularly well adapted to the form of the soft palate. In addition, it can be achieved as a result that the implant is more bendable in the vicinity of its distal end than in the region of the middle portion or the proximal portion.

In some embodiments it is provided that at least part of the implant has an ingrowth structure for the growing in of body tissue. Such growing in of body tissue leads to a better connection between the implant and the palate. In particular, the ingrowth structure may comprise a texture and/or at least one perforation. With preference, the proximal portion and/or the distal portion has/have an ingrowth structure.

Alternatively or in addition, the implant may have means for connecting to the hard palate, in particular at least one receiving opening for a bone screw. With preference, the proximal portion of the implant comprises at least one such receiving opening. A bone screw may be inserted through a receiving opening arranged there and be fixed to the hard palate. This ensures particularly stable fixing of the implant to the soft palate. This fixing may only take place temporarily (for example only until the definite healing of a wound) or else permanently.

Moreover, the distal portion may comprise at least one barb, which extends away from the distal end of the implant. Such a barb serves for improved anchoring of the distal portion in the soft palate of a patient. Furthermore, it may prevent the implant from being dislocated when the implant is inserted. Alternatively or in addition, the proximal portion may comprise such a barb, with the aid of which a dislocation of the implant can be prevented.

In some embodiments, the implant comprises a metal, in particular a biocompatible metal, or consists of a metal, in particular a biocompatible metal. In particular, it may be a metal alloy with resilient properties, such as for example NIVAFLEX® 45/18 (a curable cobalt-nickel-chromium-based resilient material, available from VACUUMSCHMELZE GmbH and Co. K G, Hanau, Germany), NITINOL (a titanium-nickel-based shape memory alloy, available for example from Johnson Matthey & Brandenburger A G, Zürich, Switzerland) or MP35N (a nickel-cobalt alloy, available from the company Hempel Special Metals A G, Dübendorf, Switzerland). Both NITINOL and MP35N have resilient and anticorrosive properties that are advantageous for the purposes of the invention and are, moreover, authorized as medical materials. Implants which comprise metal or consist thereof may be produced, for example, by lasering, etching or punching.

In the embodiments in which the implant comprises a metal or consists thereof, it preferably has a thickness of 0.05 mm to 0.5 mm, particularly preferably of 0.09 mm to 0.1 mm. If such an implant comprises a texture, this may be formed, for example, by sand blasting or etching, as known per se, for example in the production of dental implants. Alternatively, there may also be one or more perforations, which may be made for example by punching. Furthermore, the ingrowth structure may also comprise a mesh- and/or grid-like structure. Moreover, the surface of the implant may also be variably roughened.

Alternatively or in addition, the implant may comprise a plastic, in particular a biocompatible plastic, or consist thereof. Possible biocompatible plastics for this are PBI, PI, TPI, PAI, PEK, PEEK, LCP, PPS, PES, PPSU, PTFE, PFA, PEI, PSU, ETFE, PCTFE, PPP, PC-HT, PVDF, PA 46, PA 6/6T, PC, PET, PA 66, 6-3-T, PBT, PA 6, POM, PMP, PA 12, PA 11, PPE, PMMA, PS, ABS, SAN, PP and PE. With preference, the plastic has long-term strength properties, i.e. the plastic can withstand dynamic loads without suffering any appreciable effects of fatigue or failure and durably retain its elasticity and strength.

Implants according to the invention which comprise these plastics or consist thereof may be produced, for example, as an injection-molded part.

According to one possible embodiment, the implant comprises a core of a metal in the inner region and a shell of a plastic in the outer region. In these embodiments, the core of metal substantially provides the desired bending strength and resilient property of the implant, while the shell provides the flexibility of the surface, and consequently ensures better adaptability to the palate and improved biocompatibility. Such a shell is particularly suitable if the metal is not itself biocompatible, though it has the resilient properties suitable for the invention. Here the core may comprise a metal alloy or consist of such an alloy, such as for example one of those mentioned above. The shell may also comprise one of the aforementioned plastics or consist of such a plastic.

In the embodiments in which the implant comprises a biocompatible plastic or consists thereof or comprises a core of metal and a shell of plastic, the implant has with preference a thickness of 0.1 mm to 3 mm, preferably of 0.2 mm to 1.5 mm, particularly preferably of 0.3 mm to 0.6 mm.

In the embodiments in which the implant comprises a biocompatible plastic or consists thereof or comprises a core of metal and a shell of plastic, any desired structures may be machined into the injection mold that is used for the production of the implant, whereby an ingrowth structure is achieved in the implant. Alternatively, like metals, the plastic may also be subsequently machined on the surface. Alternatively, the surface of the implant may also have a fibrous braid of a biocompatible plastic.

A further aspect of the invention relates to a set of implants with at least a first implant according to the invention. In a first embodiment, the set of implants includes at least a second implant, which is different from the first implant. The implants may in this case differ, for example, in their dimensions (length, width, thickness, curvatures and/or angles in the inserted form), in their materials and/or in their bending strengths. Such a set of implants allows the surgeon to select an implant with the desired properties, as required and as appropriate for the individual anatomy of the patient to be treated.

The invention also relates to a selection process for selecting an implant from the set of implants according to the invention, which includes the following steps:

a) establishing the condition of the hard palate and the soft palate of a patient, in particular the dimensions and/or the elastic properties of the hard palate and the soft palate of the patient;
b) selecting an implant in dependence on the finding established in step a).

The implant may, for example, be selected on the basis of the following criteria:

The length of the proximal portion of the implant is between 10 and 50% of the total horizontal length of the hard palate in the median plane, or a plane parallel to it, in which the implant is to be inserted.

The length of the distal portion of the implant is between 30% and 90%, preferably between 60% and 80%, of the length of the soft palate in the median plane, or a plane parallel to it, in which the implant is to be inserted.

The angle at which the distal portion is arranged in relation to the proximal portion in the inserted form deviates from the angle between the hard palate and the soft palate when the patient is in a standing position by less than 20°, preferably by less than 10°, particularly preferably by less than 5°.

The dimensions of the palate may in this case be respectively determined directly on the patient or, for example, by means of an x-ray image. The length of the proximal portion is determined in accordance with the intended positioning of the implant. If, for example, the implant is intended to be inserted parauvularly, the length of the soft palate is likewise determined parauvularly, the uvula not contributing to the length.

Other possible criteria on the basis of which the implant may be selected comprise the thickness of the soft palate, which can be established for example by means of an x-ray image;

the result of a palpation of the soft palate;

the thickness and configuration of the bone of the hard palate, which can be established for example by means of an x-ray image;

the thickness and condition of the mucous membrane over the hard palate, which may be the result of inspection and palpation or which may be established for example by an x-ray image;

the pressure gradient behind the soft palate, which may be established for example by a nighttime manometry of the upper airways;

the prominence of the obstruction, which may be established for example by a drug-induced sleep endoscopy.

Moreover, the selection of an implant may also be made with the aid of a so-called "sizer". This is a dummy implant, which is temporarily placed on the palate to estimate the size. The use of such dummy implants for size determination per se is usual in the selection of middle ear prostheses for example.

An implant according to the invention may, for example, be inserted into a human palate according to the following method of insertion:
a) carrying out an incision, in particular a transversal incision, in the soft palate of a patient;
b) introducing the implant through the incision.

The implant may, for example, be introduced by an insertion device, for example by a trocar system or a similar system. The length of the incision is made to match the width of the implant. With preference, the length of the incision is therefore of approximately the same size as the width of the implant. The incision is carried out at a point whose distance from the transition from the hard palate to the soft palate is adjusted to the length of the distal portion of the implant, in particular at a point whose distance from this transition is approximately equal to the length of the distal portion of the implant. Optionally, the implant may be connected to the hard palate, for example by inserting a bone screw into a receiving opening of the implant and fixing it to the hard palate.

According to some methods of insertion, only a single implant is inserted into the palate of a patient. With preference, the implant is then inserted approximately medially. According to other embodiments of the method of insertion, it is also possible for two or more implants to be inserted, at least one being inserted paramedially.

In other embodiments of the set of implants, the set may include not only a first implant according to the invention but also at least one insertion device for inserting the first and/or second implant and/or at least one sizer, as described above, for estimating the size of an implant to be inserted.

The invention is presented below on the basis of several exemplary embodiments and drawings, in which FIGS. 1*a* and *b* show a first implant according to the invention, with a straight proximal portion and a straight distal portion.

Figure 1A:
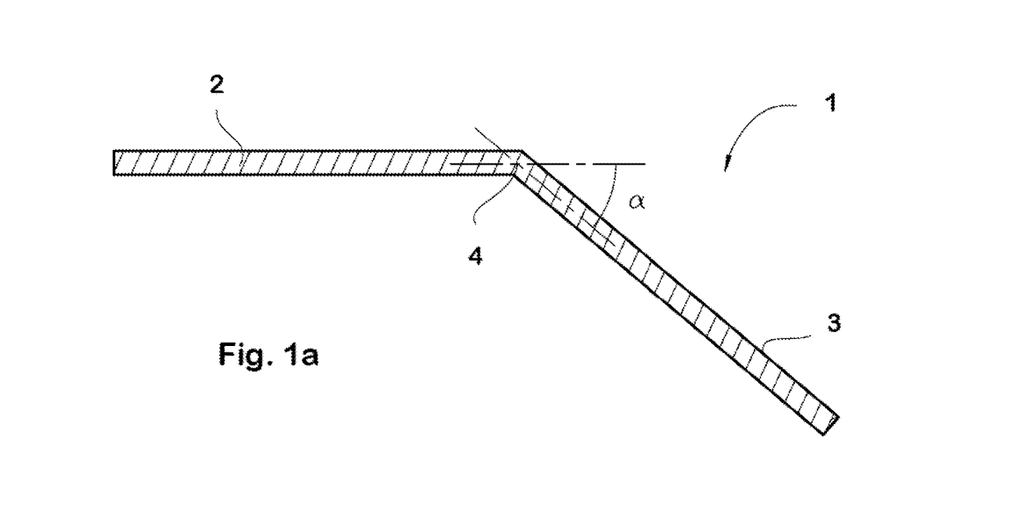
Figure 1B:
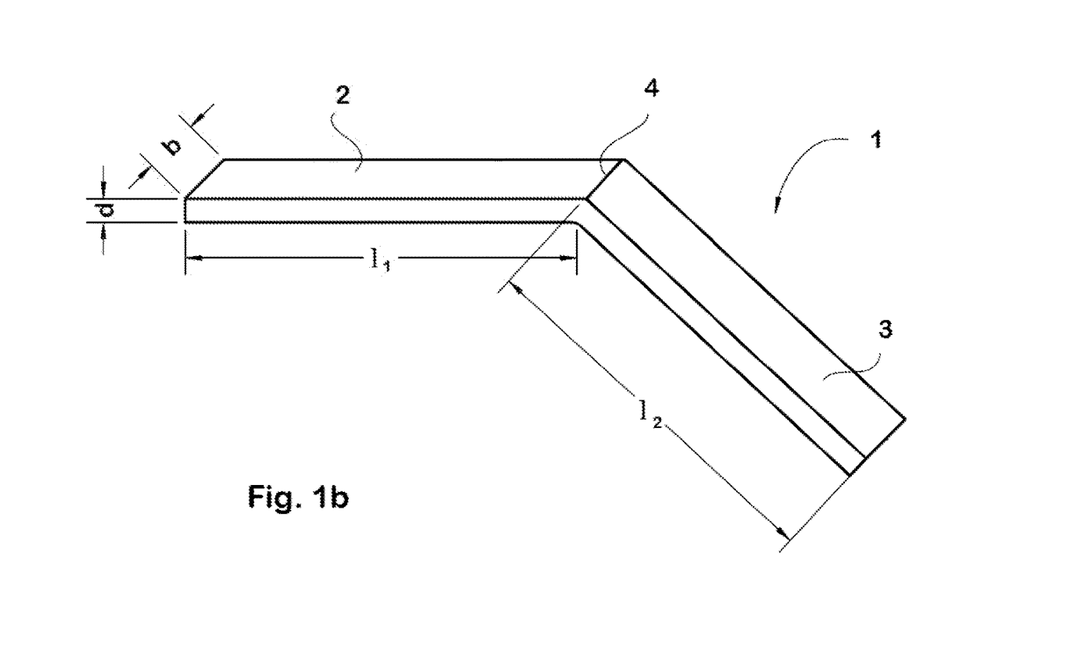
Figure 3:
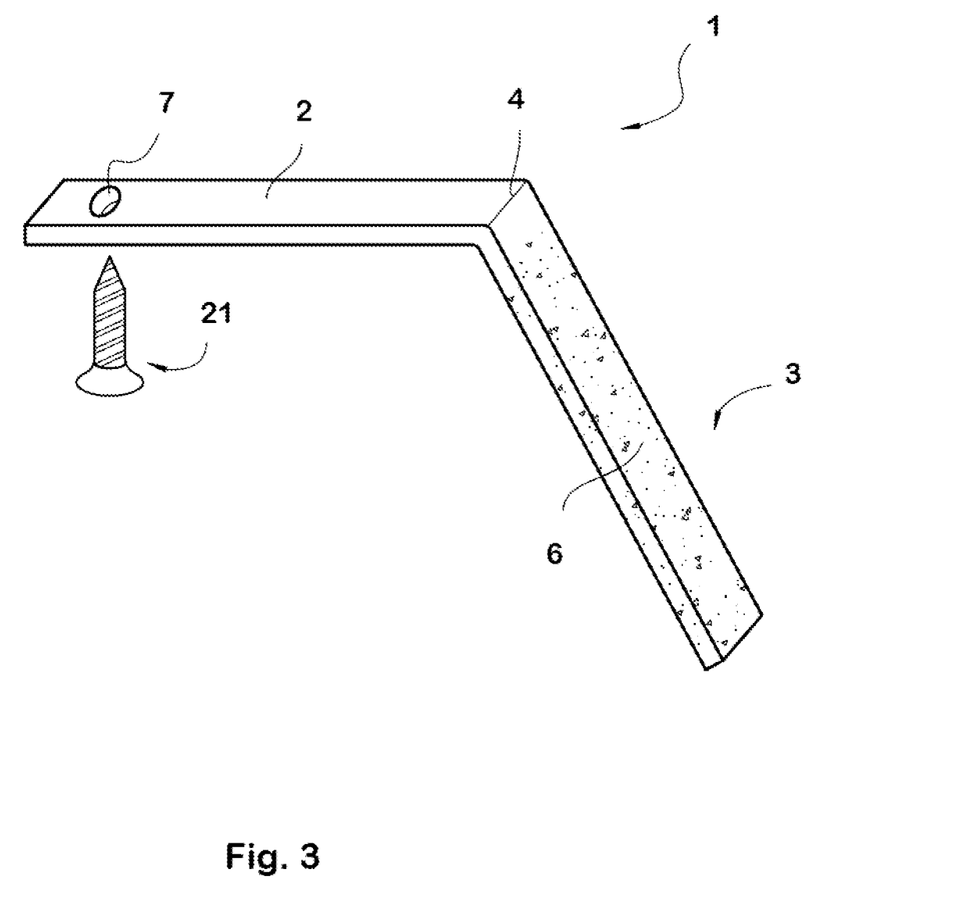
FIG. 3 shows a further implant according to the invention, with a receiving opening for a bone screw and an ingrowth structure.
Figure 9:
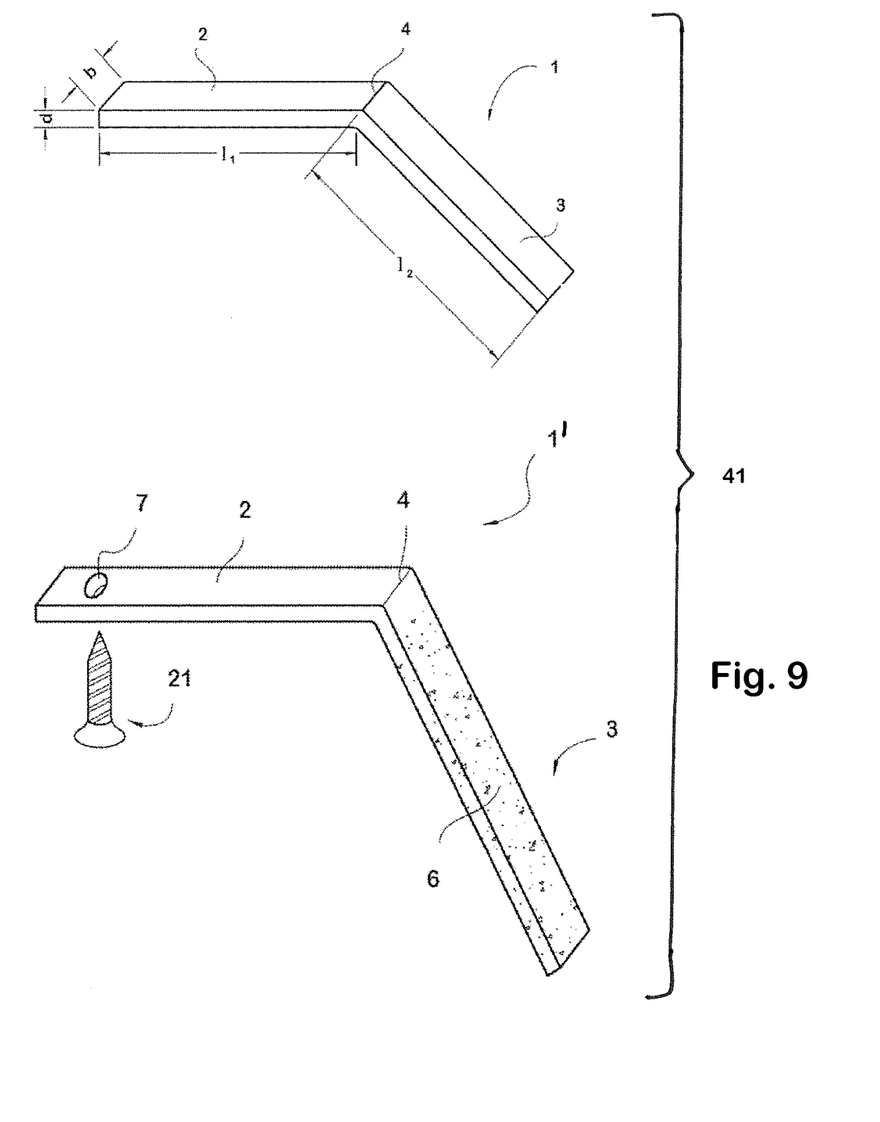

FIG. 9 shows a first set 41 comprising the implant according to FIGS. 1*a* and 1*b* as a first implant 1 and the implant of FIG. 3 as a second implant F. The second implant 1' is different from the first implant 1.

Figure 10:
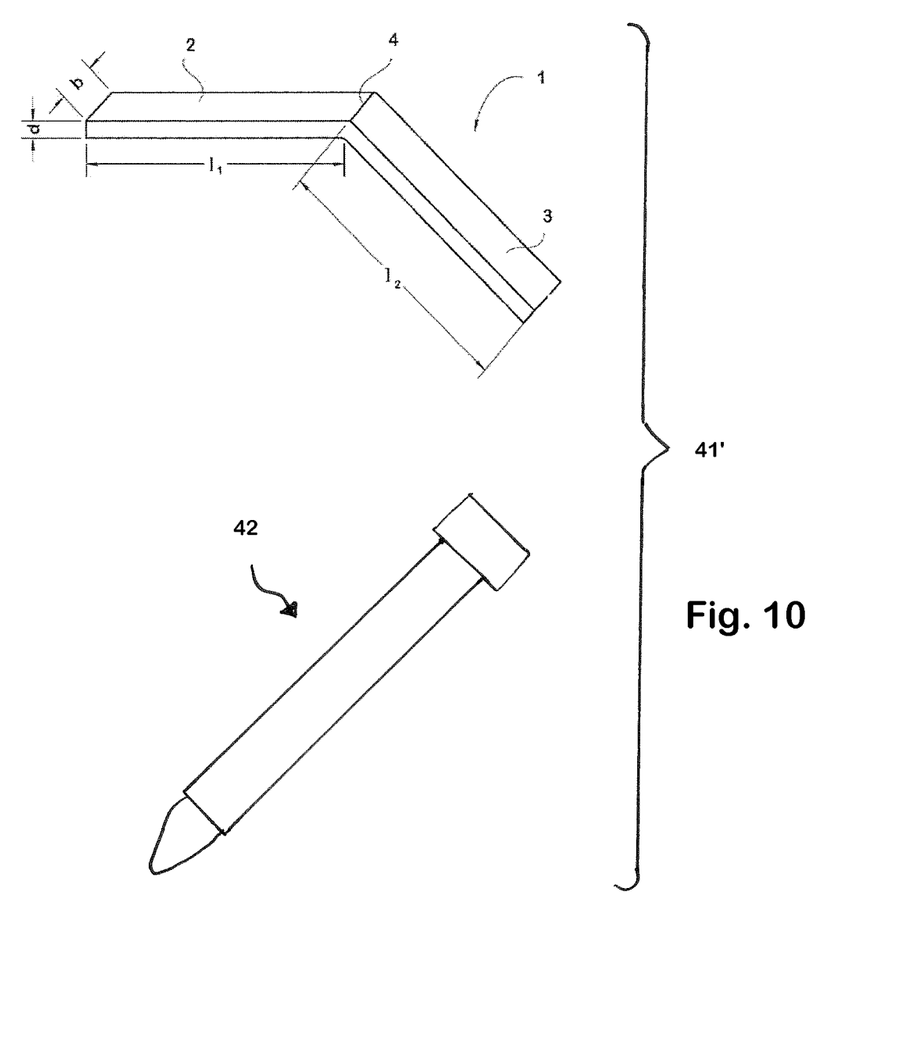

FIG. 10 shows a second set 41', which comprises the implant 1 according to FIGS. 1*a* and 1*b* and an insertion device 42 for inserting the implant 1; the insertion device is only shown schematically.

Figure 11:
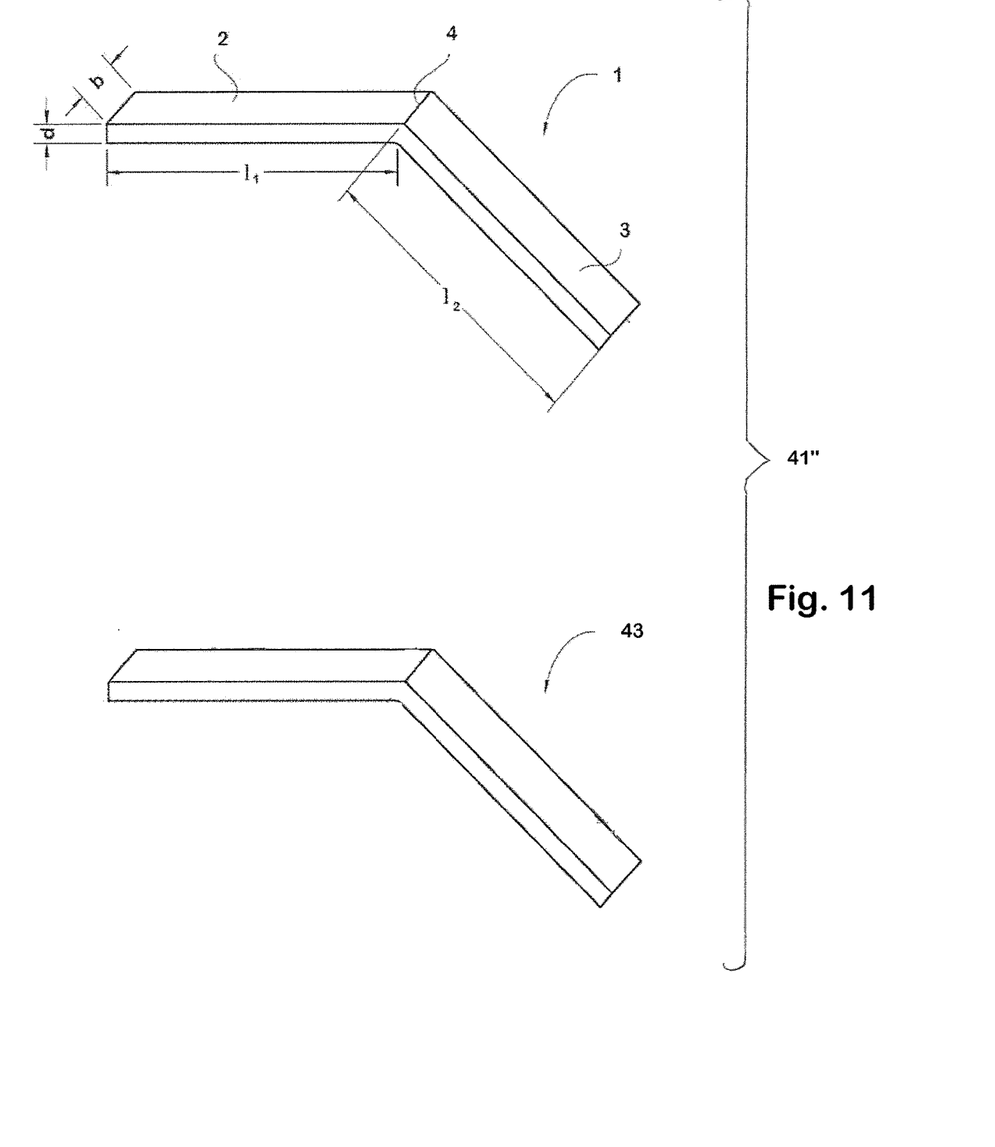

FIG. 11 depicts a third set 41" comprising the implant 1 according to FIGS. 1*a* and 1*b* and a sizer 43 for estimating the size of the implant 1 to be inserted. The sizer 43 is a dummy implant, which can be temporarily placed on a palate to estimate the appropriate size of the implant 1.

FIG. 1*a* shows an implant 1 according to the invention for a human palate in a sectional view. The implant 1 is in the form of a strip and comprises a proximal portion 2, a distal portion 3 and a middle portion 4, which extends between the proximal portion 2 and the distal portion 3. The proximal portion 2 is dimensioned in such a way that it can be fixed to a hard palate (cf. the bottom of FIG. 8). The distal portion 3 is dimensioned in such a way that it can be accommodated completely in a soft palate. In the inserted form represented in FIG. 1*a*, the distal portion 3 is arranged at an angle α of 40° in relation to the proximal portion 2.

The plane of the drawing of FIG. 1*a* forms a sectional plane of the implant 1, through which the proximal portion 2 and the distal portion 3 extend. In this sectional plane, both the proximal portion 2 and the distal portion 3 are straight. For the purposes of the invention, they are therefore assigned the curvature zero at each of their points. The middle portion 4 is formed by a kink, to which a curvature of infinity is assigned. For the purposes of the invention, therefore, the curvature of the middle portion 4 is greater than the curvature of the proximal portion 2 at each of the points of the proximal portion 2 and likewise greater than the curvature of the distal portion 3 at each of the points of the distal portion 3.

FIG. 1b shows the implant 1 of FIG. 1a in a perspective view. Both the proximal portion 2 and the distal portion 3 have a length $l_1$ and $l_2$ of respectively 20 mm. The width b of the implant 1 is 2 mm, and its thickness d is 1 mm.

The implant according to FIGS. 1a and 1b consists of a NITINOL metal alloy. The implant is elastic in such a way that the distal portion 3 is resilient in relation to the proximal portion 2. The implant 1 inserted into a palate (cf. FIG. 8) can consequently bring about the effect that a patient's soft palate as a whole is stiffened and is fixed at a substantially stable angle, while however elastic movement of the soft palate is still made possible. The implant 1 is, in particular, elastic in such a way that the pressures typically occurring behind the soft palate during swallowing, of approximately 50-100 cm water column, can still be overcome by an average palate musculature.

Figure 2:
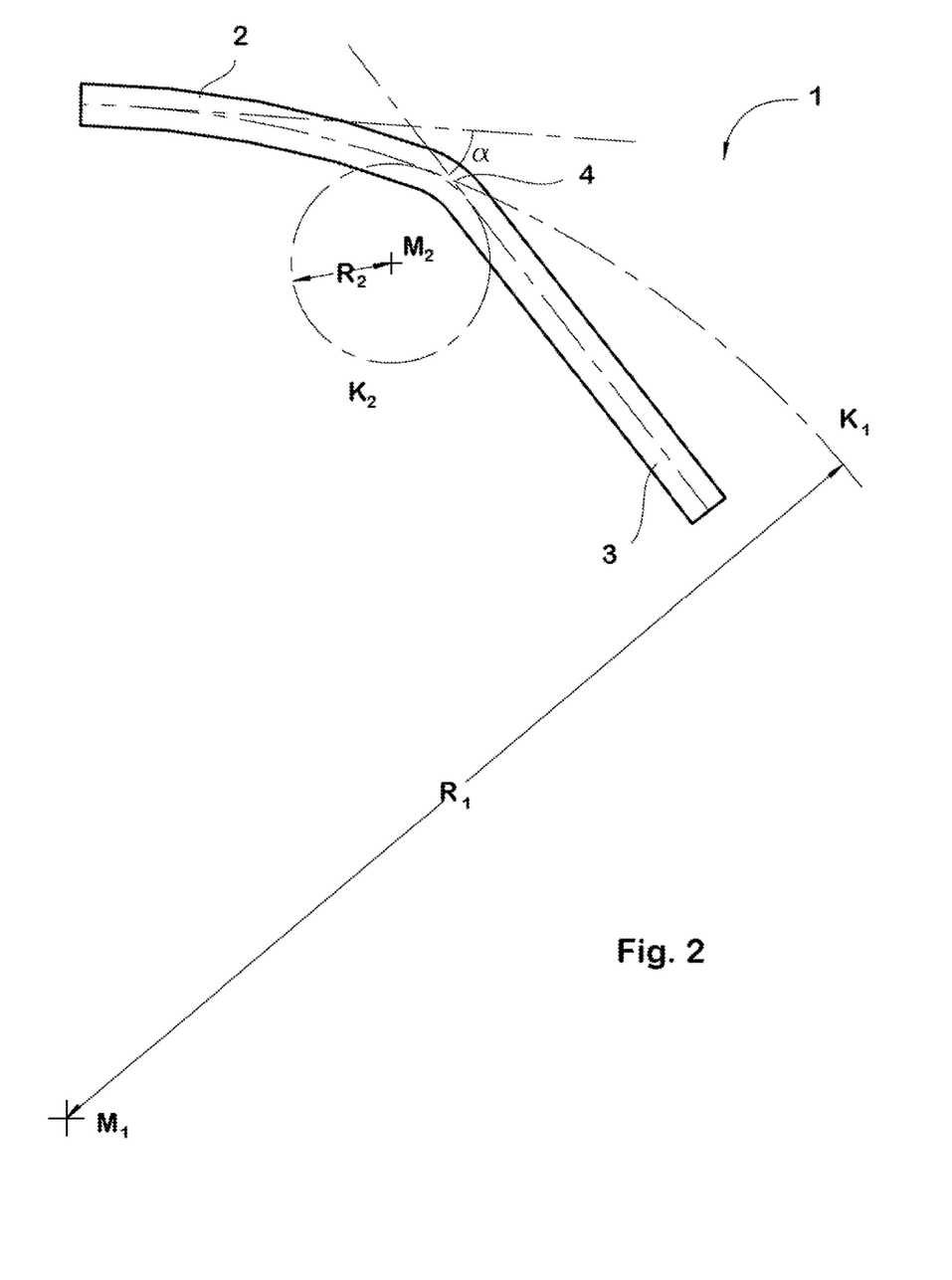
FIG. 2 shows a further implant according to the invention, with a straight distal portion, a curved proximal portion and a more curved middle portion.

The implant 1 represented in FIG. 2 is likewise in an inserted form and comprises a straight distal portion 3, but a curved proximal portion 2. The proximal portion 2 has a curvature of 0.2 cm$^{-1}$, which corresponds to the inverse of the radius $R_1$ of 50 mm of an osculating circle $K_1$, which osculates the proximal portion 2. Between the proximal portion 2 and the distal portion 3 there extends a middle portion 4, which is likewise curved. This middle portion 4 of the implant 1 is osculated by a further osculating circle $K_2$ with a radius $R_2$ of 5 mm, the inverse of which determines the curvature of 2 cm$^{-1}$ of the implant 1 in the middle portion 4. The radius $R_2$ is less than the radius $R_1$, with the result that the curvature at each of the points of the middle portion 4 is greater than the curvature of the proximal portion 2 at each of its points and greater than the curvature of the distal portion 3 at each of its points.

It goes without saying that it is also conceivable and within the scope of the invention that (as a departure from FIG. 2) the proximal portion 2 is straight and the distal portion 3 is curved.

FIG. 3 shows a further implant 1 according to the invention, in an inserted form. The implant 1 comprises a proximal portion 2, a distal portion 3 and a kink located in between, which forms a middle portion 4. The proximal portion has a receiving opening for a bone screw 21, with the aid of which the implant 1 can be fixed to a hard palate. The distal portion 3 comprises an ingrowth structure 6, which is formed by a texture. In the case of the inserted implant 1, this texture allows the growing in of body tissue, whereby the implant 1 is connected more stably to the palate.

Figure 4:
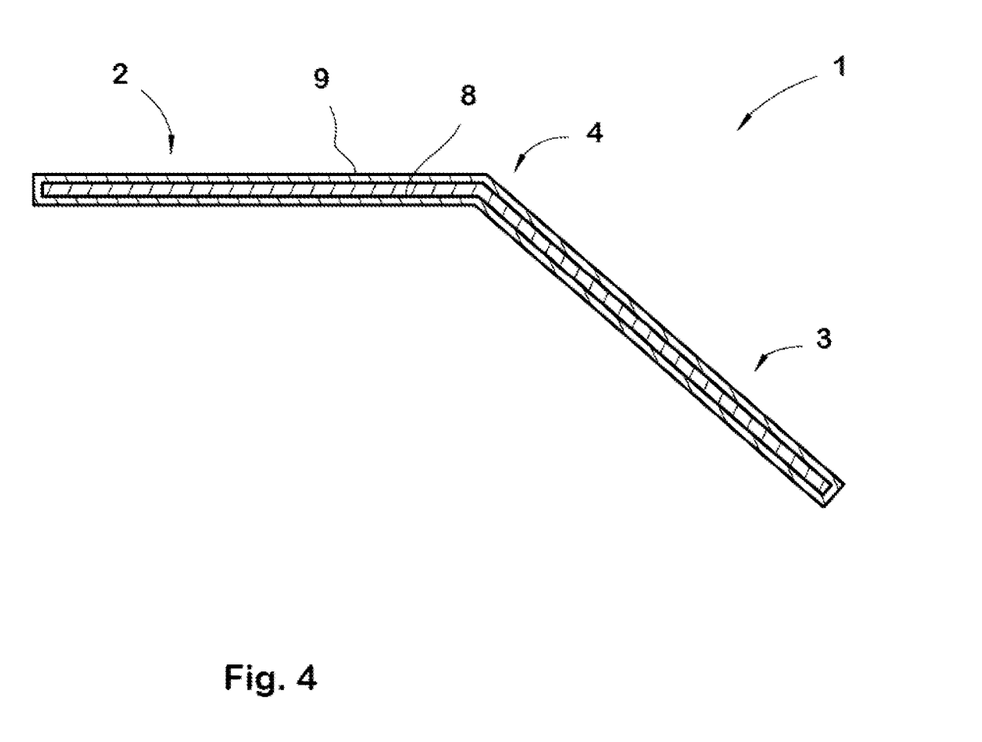
FIG. 4 shows a further implant according to the invention, with a core of metal and a shell of plastic.

A further embodiment of the implant 1 according to the invention is represented in the sectional view of FIG. 4. This implant 1, which is likewise represented in an inserted form, comprises a core 8 of NITINOL in the inner region. In the outer region, this core 8 is enclosed by a shell, which consists of PPSU.

Figure 5A:
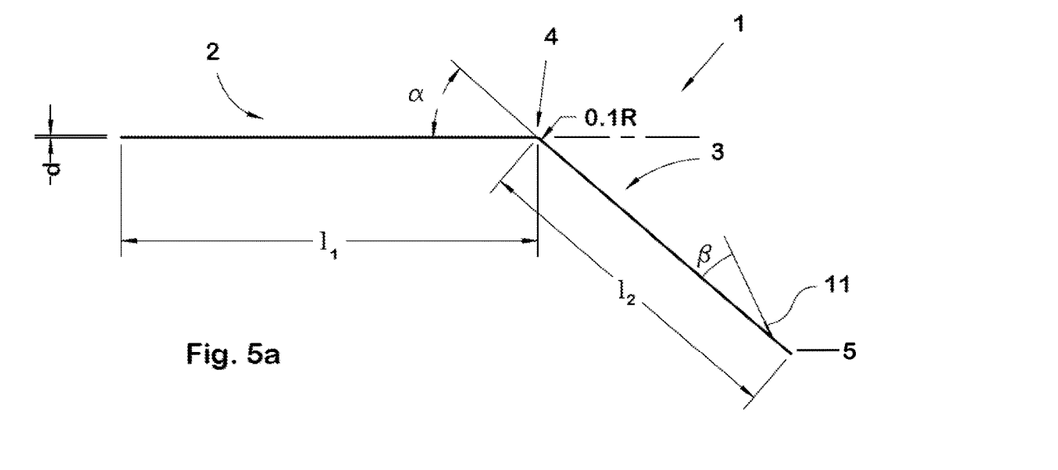
FIGS. 5*a-c* show a further implant according to the invention, with a barb.
Figure 5B:
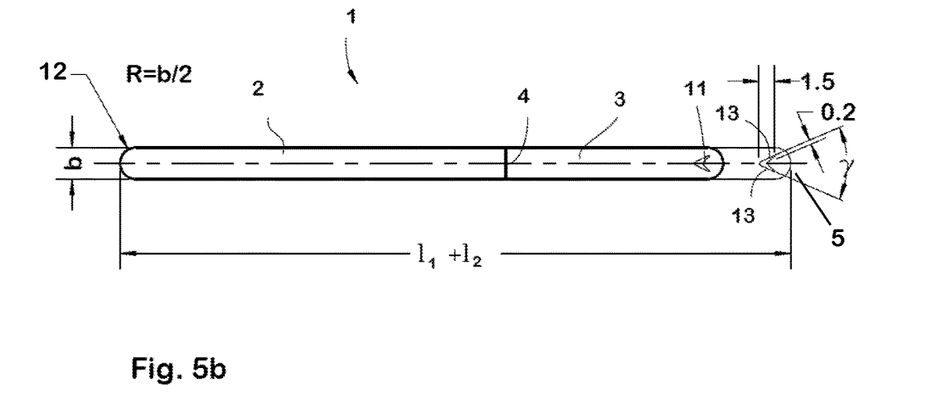
Figure 5C:
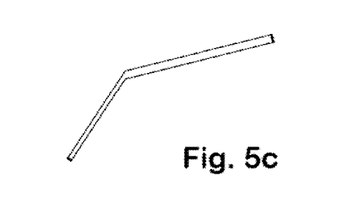

In FIGS. 5a-c, a further embodiment according to the invention of an implant 1 is shown. FIG. 5a represents a side view of the implant 1 in its inserted form. The implant 1 has a thickness d of 0.05 mm. The proximal portion 2 has a length $l_1$ of 25 mm, while the distal portion 3 has a length $l_2$ of 20 mm. The angle α formed between the proximal portion 2 and the distal portion 3 is 40°. The middle portion 4 is formed as a kink with a radius of 0.1 mm, which corresponds to a radius of curvature of 100 cm$^{-1}$.

In FIG. 5a, a barb 11 can be seen. This extends away from a distal end 5 of the implant 1 at an angle β of 20° to the distal portion 3. The barb 11 has the form of a triangle, one side of which forms a kink in the direction of the width of the implant 1 and the two other sides of which are free. The two free sides converge at a tip of the barb 11. The two free sides of the barb 11 may be produced by punching or etching into the free distal portion 3 two slits 13 of 0.2 mm in width, which are arranged at an angle γ of 40° in relation to one another and converge at a point (cf. also FIG. 5b). The barb 11 serves for improved anchoring of the distal portion 3 in the soft palate of a patient. Furthermore, the barb 11 can prevent dislocation of the implant 1 during insertion. Furthermore, it is possible to provide a similar barb at the proximal end, in order to prevent dislocation of the implant.

In FIG. 5b, the implant 1 is shown in a plan view. Both the proximal end 12 and the distal end 5 of the implant 1 are rounded in a semicircular form. As a result, sharp edges are avoided, which makes the insertion of the implant 1 into a palate easier and also more pleasant for the patient. The solid delimiting line of the implant 1 in FIG. 5b shows the outline in the kinked inserted form, while the dash-dotted delimiting line reproduces the outline in a flat ready form.

FIG. 5c shows the implant 1 in a perspective view.

Figure 6A:
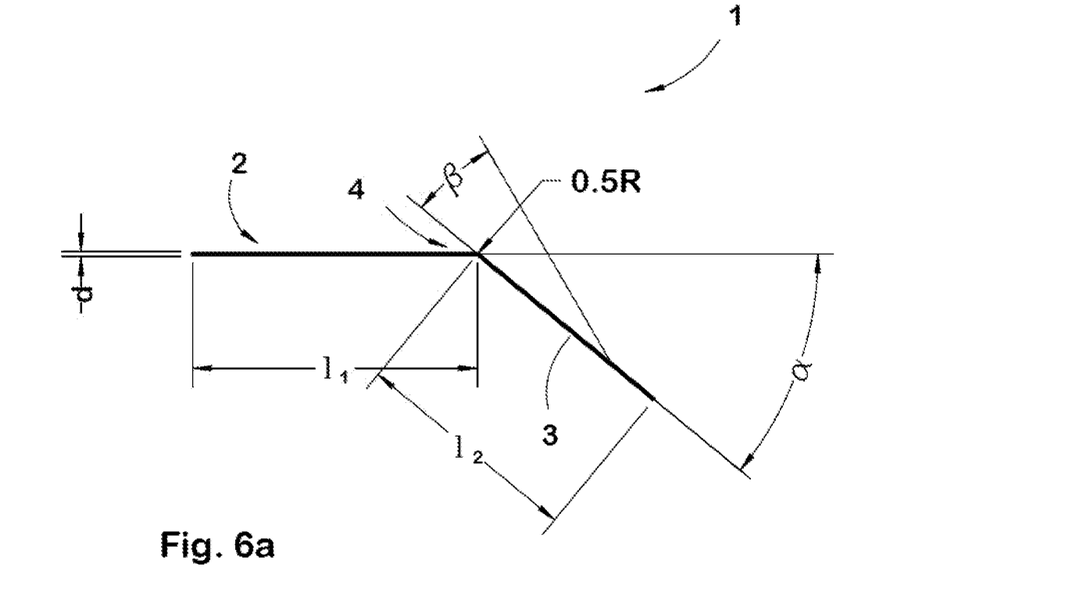
FIGS. 6*a* and *b* show a further implant according to the invention, with a barb and a constriction.
Figure 6B:
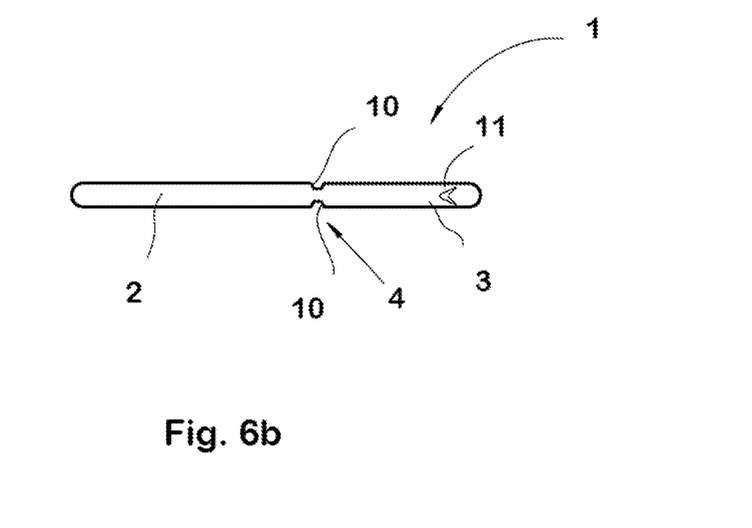

In FIGS. 6a and b, a further implant 1 according to the invention is shown in a side view and a plan view, respectively. This implant 1 differs from that shown in FIGS. 5a-c by a constriction 10 in the middle portion 4, which forms an intended deformation region. This constriction 10 defines a position at which the implant 1 can be bent and/or kinked, in order to transfer it from a ready form into an inserted form.

Figure 7:
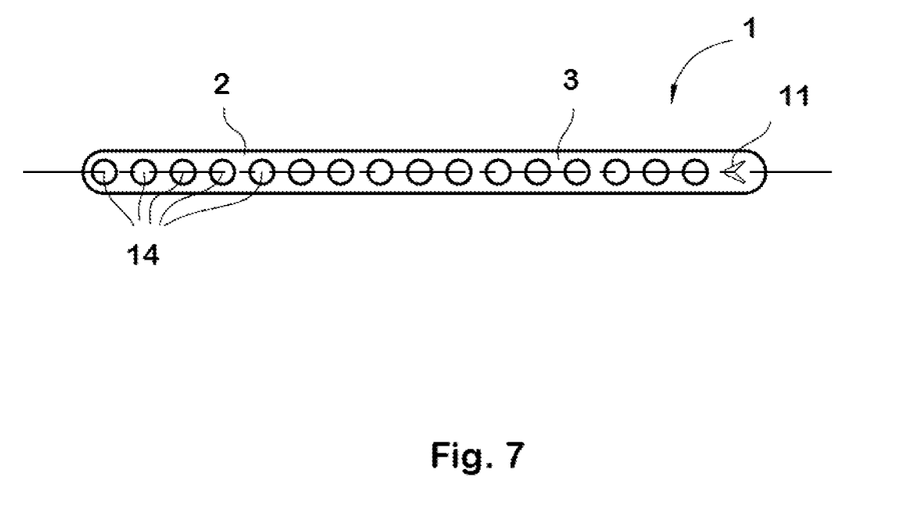
FIG. 7 shows a further implant according to the invention, with a barb and an ingrowth structure.

In FIG. 7, a further implant 1 according to the invention, which is in a flat ready position, is represented. From this ready position, it can be brought into an inserted form by bending or kinking. This implant also has a barb 11, which coincides with those shown in FIGS. 5a-c as well as 6a and b. Furthermore, the implant 1 comprises a number of circular, equidistant perforations 14, altogether 16, which penetrate the implant and form an ingrowth structure for the growing in of body tissue, whereby the implant 1 can be connected more stably to the palate.

Figure 8:
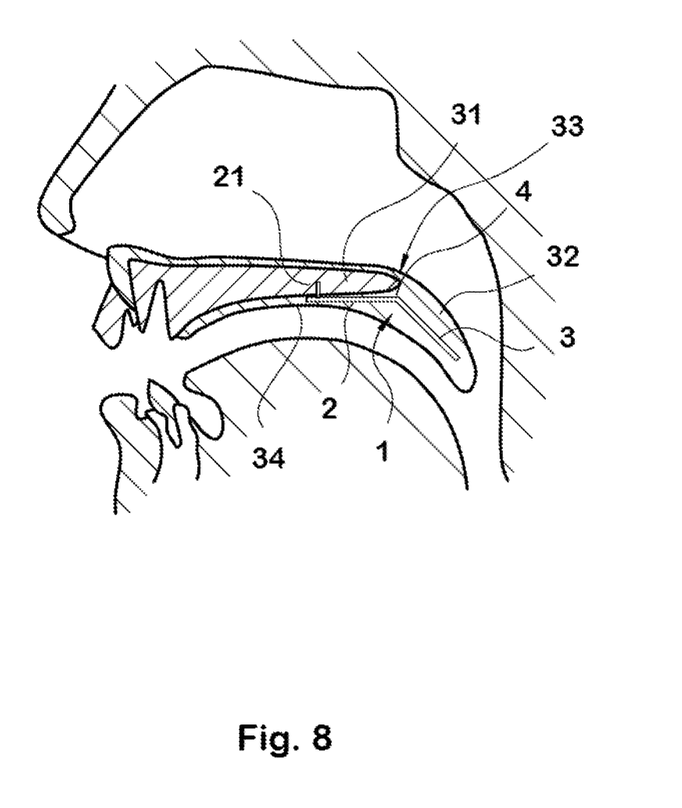
FIG. 8 shows an implant according to the invention, inserted into a human palate.

FIG. 8 shows part of a human head in a sectional representation. The palate comprises a hard palate 31 and a soft palate 32. Inserted into the palate is an implant 1 according to the invention, in the inserted form. In this case, the proximal portion 2 of the implant 1 is fixed to the hard palate 31 along its entire length. This is possible on account of the small curvature of the proximal portion 2 in comparison with that of the middle portion 4. The proximal portion 2 is additionally fixed to the hard palate 31 with the aid of a bone screw 21. The distal portion 3 of the implant 1 is completely accommodated in the soft palate 32 and extends approximately along two thirds of the length thereof. Between the proximal portion 2 and the distal portion 3, the implant 1 has an edge which forms a middle portion 4. This middle portion 4 is arranged in the region of the transition 33 from the hard palate 31 to the soft palate 32. To insert the implant 1, it may be introduced into an incision 34 previously carried out.

On account of the fixing of the proximal portion 2 to the hard palate 31, the distal portion 3 of the implant 1, and consequently the soft palate 32, is/are also kept at an angle in relation to the hard palate 31. When the patient is in a lying position, the soft palate 32 consequently cannot fall back into the area of the throat in an adverse way. On account of the elasticity of the implant 1, however, the distal portion 3 is resiliently mounted in relation to the proximal portion 2, with the result that the soft palate 32 is also resiliently mounted in relation to the hard palate 31. Thus, for example, speaking and swallowing are not significantly hindered.

A set of implants according to the invention, which is not graphically represented, may include, for example, implants with some or all of the possible combinations of the following dimensions:

width of the implant: 2 mm, 3 mm, 5 mm;
length of the proximal portion: 20 mm, 25 mm;
length of the distal portion: 20 mm;
angle between proximal portion and distal portion: 30°, 35°, 40°, 45°, 50°;

Consequently, there are altogether 3 times 2 times 5, that is to say 30, possible variants of the implant within this set of implants.

We claim:

1. An implant adapted for use in a palate, in particular a human palate, said implant comprising
    a distal portion dimensioned so as to be completely accommodated in a soft palate, and
    a proximal portion dimensioned so as to be fixed to a hard palate, and
    a middle portion extending between the proximal portion and the distal portion,
    wherein the implant is elastic in the middle portion in such a way that the distal portion is resilient in relation to the proximal portion, and
    the proximal portion extends at an angle of between 15° and 75° in relation to the distal portion.

2. The implant as claimed in claim 1, wherein the middle portion has an intended deformation region, at which the middle portion can be deformed.

3. The implant as claimed in claim 1, wherein at least part of the implant has an ingrowth structure for the growing in of body tissue.

4. The implant as claimed in claim 1, wherein the implant comprises a shape memory material or consists thereof, and at an inserted temperature of between 35° C. and 40° C. is in the inserted form.

5. The implant as claimed in claim 1, further comprising means for connecting the implant to the hard palate.

6. The implant as claimed in claim 1, wherein the implant comprises or consists of plastic.

7. The implant as claimed in claim 1, wherein the implant is substantially in the form of a strip.

8. The implant as claimed in claim 1, wherein the proximal portion has a length ($l_1$) of 15 mm to 30 mm.

9. The implant as claimed in claim 1, wherein the distal portion has a length ($l_2$) of 15 mm to 25 mm.

10. A set of implants comprising at least two implants, wherein a first implant of said implants and a second implant of said implants are each according to claim 1, the second implant being different from the first implant.

11. A set of implants including at least two implants, wherein at least one implant of said implants is according to claim 1, as well as at least one insertion device for inserting the implant.

12. A set of implants including at least two implants, wherein at least one implant of said implants is according to claim 1, as well as at least one sizer for estimating the size of an implant to be inserted.

13. The implant as claimed in claim 1, wherein the implant comprises a metal.

14. The implant as claimed in claim 1, wherein the implant has an inner metal core and an outer plastic shell.

15. A method for selecting, from a set of different implants, an implant adapted for use in a palate, in particular a human palate, each said implant comprising
    a distal portion dimensioned so as to be completely accommodated in a soft palate, and
    a proximal portion, dimensioned so as to be fixed to a hard palate, and
    a middle portion extending between the proximal portion and the distal portion,
    wherein the implant is elastic in the middle portion in such a way that the distal portion is resilient in relation to the proximal portion,
    which method comprises the following steps:
    a) establishing the condition of the hard palate and the soft palate of a patient; and
    b) selecting an implant in dependence on the finding established in step a).

* * * * *